(12) United States Patent
Avent et al.

(10) Patent No.: US 7,707,751 B2
(45) Date of Patent: May 4, 2010

(54) ADJUSTABLE ORTHOTIC

(75) Inventors: Richad T. Avent, Memphis, TN (US); Philip C. Yang, Memphis, TN (US); Charles E. Lundy, Jr., Germantown, TN (US)

(73) Assignee: Schering-Plough Healthcare Products, Inc., Memphis, TN (US)

( * ) Notice: Subject to any disclaimer, the term of this patent is extended or adjusted under 35 U.S.C. 154(b) by 734 days.

(21) Appl. No.: 11/454,701

(22) Filed: Jun. 16, 2006

(65) Prior Publication Data

US 2007/0289170 A1  Dec. 20, 2007

(51) Int. Cl.
*A61F 5/14* (2006.01)
*A43B 13/38* (2006.01)

(52) U.S. Cl. .................. 36/150; 36/159; 36/44
(58) Field of Classification Search .......... 36/150, 36/44, 155–165, 43
See application file for complete search history.

(56) References Cited

U.S. PATENT DOCUMENTS

| | | | |
|---|---|---|---|
| 1,517,170 A | 11/1924 | Rosenthal |
| 1,690,964 A | 11/1928 | Balsakas |
| 1,867,431 A | 7/1932 | Wood |
| 2,065,290 A | 12/1936 | Rigandi |
| 2,068,786 A | 1/1937 | Balaskas |
| 2,139,971 A | 12/1938 | Pava |
| 2,224,590 A | 12/1940 | Boivin |
| 2,307,416 A | 1/1943 | Margolin |
| 2,404,731 A | 7/1946 | Johnson |
| 2,585,692 A | 2/1952 | Scholl |
| 2,713,215 A | 7/1955 | Cosneck |
| 2,713,732 A | 7/1955 | Guest |
| 2,716,295 A | 8/1955 | Stein |
| 2,826,834 A | 3/1958 | Ratcliff |
| 3,081,774 A | 3/1963 | Leyveld |
| 3,084,695 A | 4/1963 | O'Donnell |
| 4,338,734 A | 7/1982 | Schwartz |
| 4,541,184 A | 9/1985 | Leighton |
| 4,739,765 A * | 4/1988 | Sydor et al. .................. 36/174 |
| D295,690 S | 5/1988 | Finn |
| 4,791,736 A | 12/1988 | Phillips |
| 4,813,157 A | 3/1989 | Boisvert et al. |
| 4,841,648 A | 6/1989 | Shaffer et al. |
| 5,101,580 A | 4/1992 | Lyden |
| 5,138,774 A | 8/1992 | Sarkozi |
| 5,187,885 A | 2/1993 | Murphy |
| 5,282,326 A | 2/1994 | Schroer, Jr. et al. |
| 5,551,173 A | 9/1996 | Chambers |
| 5,611,153 A | 3/1997 | Fisher et al. |

(Continued)

OTHER PUBLICATIONS

International Search Report for PCT/US2007/014264, mailed Feb. 1, 2008 (3pgs).

*Primary Examiner*—Ted Kavanaugh
(74) *Attorney, Agent, or Firm*—Matthew J. Golden

(57) ABSTRACT

An example orthotic is described which may include a cushioning first layer and a shell layer. The shell layer may be configured to extend longitudinally from at least the talus-navicular joint to the medial cuneiform-first metatarsal joint and laterally under at least the medial cuneiform bone when the orthotic is in use. The shell layer may be configured to receive a removable insert that alters an amount of arch support provided by the orthotic. A set of inserts may be provided to allow the example orthotic to be customized based on user support preferences.

7 Claims, 15 Drawing Sheets

U.S. PATENT DOCUMENTS

| | | |
|---|---|---|
| D391,749 S | 3/1998 | Fisher |
| D411,759 S | 7/1999 | Byrd |
| 6,000,147 A | 12/1999 | Kellerman |
| 6,105,283 A | 8/2000 | Park |
| 6,192,607 B1 | 2/2001 | Kolada |
| 6,247,250 B1 | 6/2001 | Hauser |
| 6,301,807 B1 * | 10/2001 | Gardiner .................... 36/155 |
| 6,315,786 B1 | 11/2001 | Smuckler |
| 6,557,273 B2 | 5/2003 | Polifroni |
| 6,598,319 B2 | 7/2003 | Hardt |
| 6,604,301 B1 | 8/2003 | Manoli, II et al. |
| 6,817,115 B2 | 11/2004 | Polifroni |
| 6,854,199 B2 | 2/2005 | Polifroni |
| 6,915,598 B2 | 7/2005 | Grisoni et al. |
| 6,973,743 B1 | 12/2005 | Mowery |
| 6,976,322 B1 | 12/2005 | Walker |
| 6,990,756 B1 * | 1/2006 | Johnson ...................... 36/155 |
| 2002/0007569 A1 | 1/2002 | Crane et al. |
| 2002/0092203 A1 | 7/2002 | Hardt |
| 2003/0009915 A1 | 1/2003 | Bacon |
| 2003/0150134 A1 | 8/2003 | Hardt |
| 2004/0025376 A1 | 2/2004 | Grisoni et al. |
| 2004/0103561 A1 | 6/2004 | Campbell et al. |
| 2004/0205984 A1 | 10/2004 | Hardt |
| 2004/0250450 A1 | 12/2004 | Snell et al. |
| 2005/0039351 A1 | 2/2005 | McCracken |
| 2005/0108899 A1 | 5/2005 | Kielt et al. |
| 2005/0223604 A1 | 10/2005 | Neuner |
| 2005/0235526 A1 | 10/2005 | Kim |
| 2005/0257401 A1 | 11/2005 | Axt et al. |
| 2006/0016103 A1 | 1/2006 | Green |
| 2007/0033834 A1 * | 2/2007 | Cheskin et al. ................ 36/44 |

* cited by examiner

ADJUSTABLE ORTHOTIC

BACKGROUND

Conventional footwear inserts, such as orthotics, are typically sold to customers to conform to a particular customer need. As those needs change over time, either due to the change in a customer's foot conditions or a customer's personal preferences, a customer would typically buy an entirely new replacement. This practice of buying multiple orthotics can become expensive and also bulky to store.

Off-the-shelf orthotics or insoles are generally not customizable and have a limited range of support. These orthotics are made in different sizes, but typically have a particular shape and support structure. Orthotics that are sold may vary in different properties, such as the type of material, hardness of the material, stiffness, flexibility, flexural modulus of the material, or the shape of an arch, etc. However, for a particular orthotic, each of these individual characteristics is not customizable. Thus, many variations of orthotics must be provided in a retail environment to satisfy different custom preferences.

Some custom orthotics have been described but are not easily adjustable by a user. For example, a custom orthotic may be made from a material that is molded when compressed by a foot, or made of a curable material to conform to a foot. Alternatively, a custom orthotic may be made from taking measurements of an individual's foot. However, the disadvantage of these custom orthotics is that they must be custom made with a custom fit for a particular foot. They also may not be adjusted depending on the use. For example, a user may want a different level of support when playing a sport versus everyday use.

DETAILED DESCRIPTION

Figure 1:
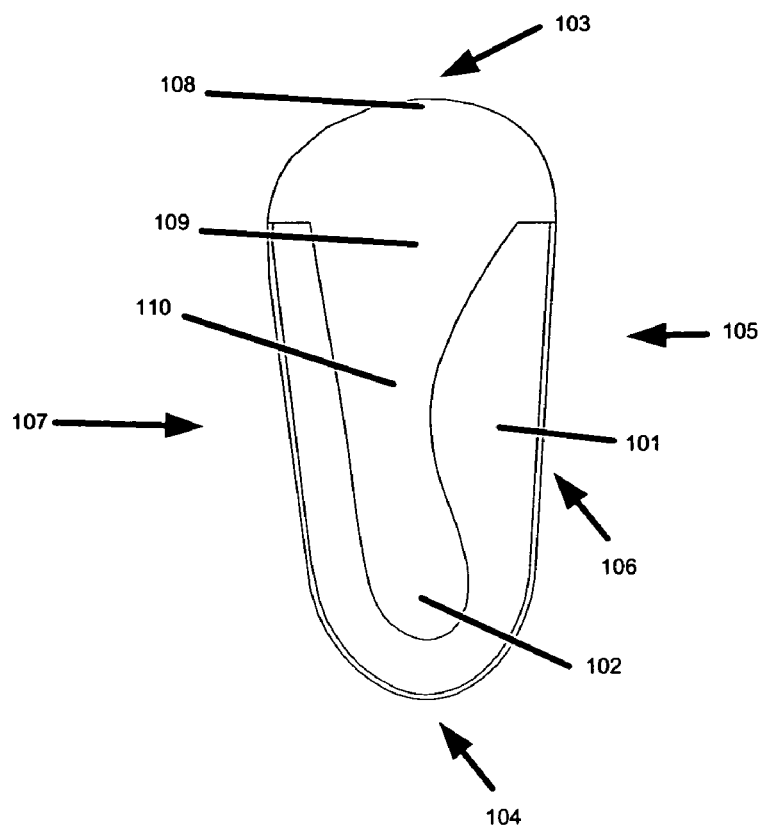
FIG. 1 illustrates a top view of an example adjustable orthotic, according to an example embodiment of the present invention.

Orthotics or insoles are typically made to provide support, such as arch support or support for various other parts of the foot. However, a user may want to customize or vary the support in the orthotic without switching to or buying a new orthotic. Retailers may also want to stock a single product that satisfies customers with different support or comfort preferences.

In some example embodiments of the present invention, an adjustable orthotic solves the problem of providing customizable levels of support by using different inserts. Some example embodiments of the present invention include orthotics configured to receive inserts, which alter the support properties of the orthotic. In one example embodiment, the location of the orthotic insert receiving location, e.g. an opening configured to receive an insert, may be located in a relatively firm shell layer under a relatively softer foam layer. The insert receiving location of the shell layer may be a designated area with apertures in which a removable insert may be received. In one example embodiment, the insert receiving location area may be longitudinally directed along the bottom center of the orthotic, supporting the arch region, a region that may provide support for the arch cavity underlying any part of the medial or lateral longitudinal arch. Alternatively, the insert receiving location area may be a space in-between a shell layer and a foam layer of the adjustable orthotic, located under a portion of the medial arch region of the foot.

One advantage of some of the example embodiments of the present invention is that they may provide multiple levels of support without having to buy new orthotics. The adjustable orthotic may be configured for different users' preferences, or for different activities, by interchanging different removable inserts. Some example embodiments of an adjustable orthotic may include a relatively soft cushioning layer with a relatively harder shell layer disposed under the first cushioning layer, the shell layer configured to extend longitudinally from at least the talus-navicular joint to the medial cuneiform-first metatarsal joint and laterally under at least the medial cuneiform bone when the orthotic is in use. The shell layer may be configured to receive a removable insert that alters an amount of support provided by the orthotic.

Some examples adjustable orthotics may contain varying features. An example adjustable orthotic may have a cover layer over a cushioning layer with a shell layer underneath the cushioning layer. A removable insert may be received by the adjustable orthotic.

Regarding the shell layer, the shell layer may be configured to support the arch of the user when the orthotic is in use; the shell layer may be made from thermoplastic urethane; the shell layer may have a shore hardness in the range of 90A to 100A or below 59D; the shell layer may have a flexural modulus range between 5 to 100 ksi; the shell layer may contain apertures (e.g. cavities, divots, etc.) to receive insertion tabs on removable inserts; the shell layer may have a cavity on a bottom surface extending longitudinally from at least the talus-navicular joint of the user to the medial cuneiform-first metatarsal joint of the user when the orthotic is in use, the opening configured to receive the removable insert; the shell layer may have a forward and rear aperture extending from the cavity through the shell layer, the apertures configured to receive insertion tabs on the removable insert; the shell layer may contain circular concave grooves along the surface; the shell layer may contain oval-shaped holes along the arch area; the shell layer may contain protruding ribs along the arch area.

Regarding the removable inserts, the removable inserts may be configured to be received by the shell layer, the removable inserts altering support provided by the orthotic when the removable inserts are received by the shell layer; the removable inserts may be harder and/or more rigid than the shell layer; the removable inserts may have a shore hardness in the range of 59D to 71D or 69D to 79D; the removable inserts may be received on the bottom of the orthotic or on the bottom of the shell layer; an upper surface of the removable inserts may convex upward towards the wearer's foot when the removable inserts are received by the shell layer; the removable inserts may include a substantially flat body with protruding ribs and the protruding ribs may extend longitudinally along the substantially flat body and shaped to curve away from each other; insertion tabs may form part of the removable inserts and may be inserted into apertures in the shell layer and removably retained in the shell layer; the removable inserts may be comprised of thermoplastic urethane (TPU) or a combination of TPU and acrylonitrile-butadiene-styrene (ABS); the removable inserts may be made from 60 to 70% TPU; the removable inserts may be made from 30 to 40% ABS; the removable inserts may be made from TPU and ABS at a ratio ranging between 7/3 to 3/2; the removable inserts may have a flexural modulus between 110 to 210 ksi, or for a firmer insert, between 220-500 ksi.

A set of different removable inserts configured to allow a user of the orthotic to customize the support properties of the orthotic by inserting a selected removable insert in the shell layer may be provided, the selected removable insert being selected from the set of different removable inserts. The set of different removable inserts may be substantially dimensionally identical but have different material properties. Alternatively, the set of different removable inserts are dimensionally different, but are made from the same material.

Regarding the cushioning layer, the cushioning layer may have a density in the range of 1.3 to 8.3 pounds per foot cubed; the cushioning layer may be made from polyurethane foam; the cushioning layer may extend longitudinally from at least the heel region to the metatarsal-proximal phalanges joint; the cushioning layer may have a deformable depression in the bottom of a heel region; the cushioning layer may extend longitudinally beyond the anterior and posterior ends of the shell layer; a heel cup may be formed as part of a heel portion of the cushioning layer; a secondary layer may be situated between the cushioning layer and shell layer; a cover layer may be situated above the cushioning layer, the cover layer made from polyester.

When the orthotic is acquired, e.g., in a purchase package, a user may also be provided with a set of inserts with varying hardness, stiffness, or dimensions. Users would be able to alter the support of their adjustable orthotic by changing the inserts on their own. For example, users without a defined arch or a low arch may need more support and may prefer greater hardness so as to provide more support for the arch of the foot. On the other hand, users with a high arch or an arch that is more defined may prefer more cushioning than hardness. A greater degree of support due to a harder or stiffer insert may even be uncomfortable to a user with a high arch because, as their arch is defined, the harder inserts may stick into the arch which may become sensitive to the hard feeling underneath the foot. Users may also want to adjust the support of their adjustable orthotic over time, for example, if the orthotic is "broken in" with use, the user may want to use a different hardness insert.

Example embodiments of an adjustable orthotic may contain varying features as well. An adjustable orthotic system may have a cushion orthotic configured to receive a removable insert in an arch region that alters an amount of support provided by the cushion orthotic and a set of removable inserts configured to be received by the cushion orthotic, each removable insert in the set of removable inserts providing a different level of support for a user of the cushion orthotic when the removable insert is inserted in the cushion orthotic. The cushion orthotic may be placed inside a shoe with or without a removable insert received by the cushion orthotic. The removable inserts in the set of removable inserts may be made from different material compositions, may be substantially dimensionally identical, may be dimensionally different, and/or may have a different respective stiffness.

Example embodiments of a procedure for providing a user with a customized fit for a cushion orthotic may also vary. The procedure may involve providing to the user a cushion orthotic that is configured to receive a removable insert in an arch region that alters an amount of support provided by the cushion orthotic, providing to the user a set of inserts with different properties, the inserts configured to be received by the cushion orthotic, and providing an instruction to the user that the user should select an insert from among the set of inserts which provides a user-preferred amount of support from the cushion orthotic when the selected insert is inserted in the cushion orthotic. The set of inserts may be substantially dimensionally identical but have different material properties. The cushion orthotic may be configured to receive the removable insert on a bottom surface of the cushion orthotic. The inserts may include insertion tabs, and the cushion orthotic may include apertures configured to receive the insertion tabs When a customer first purchases an adjustable orthotic, the customer may be provided with an orthotic, with a location for receiving a removable insert that alters an amount of support provided by the orthotic, as well as a set of inserts, the inserts varying in support levels in relation to each other, the inserts configured to be received by the shell layer. The inserts may be provided in a set so that the customer can choose different levels of hardness and/or stiffness of inserts to attach to the orthotic. A customer need not put inserts of the same hardness and/or stiffness on both feet. For example, a customer may want firm support in one foot and only medium support in the other.

The inserts may be dimensionally similar, with varying levels of support altered by the hardness and/or flexibility adapted from changing the factors such as the mixture and/or hardness of materials used. Alternatively, the inserts may also provide varying levels of support by being dimensionally different. For example, inserts of different lengths, thicknesses, or curvatures may be used to provide different levels of support.

Alternatively, the adjustable orthotic system can be sold to a customer such that a customer can buy an adjustable orthotic with a first package of inserts and later buy separate packages of inserts. This allows a customer, having an initial set of inserts to adjust support, to buy more inserts in a different package to adjust the range of support to a finer degree. Furthermore, if a customer loses a set of inserts the customer can buy a new package of inserts without needing to buy a new orthotic.

FIG. 1 illustrates a top view of an example adjustable orthotic, according to an example embodiment of the present invention. This view shows the side of the orthotic which is adjacent the foot when the example adjustable orthotic is located in a shoe worn by a user. The view illustrates the various directional orientations, including the front or distal 103 end of the orthotic and the back or proximal 104 end of the example adjustable orthotic. The particular example adjustable orthotic in FIG. 1 is shaped for a left foot. It will be appreciated that the example may be reversed along the longitudinal axis for the right foot. The medial 105 side contains a part of the medial arch region 106 and the lateral 107 side is located on the left of the figure which contains the lateral longitudinal arch.

The example adjustable orthotic may consist of a cushioning layer extending from the heel region to approximately three-quarters of the foot, underneath the metatarsal-proximal phalanges joints of a user. Alternatively, the cushioning layer may be shorter or may extend all the way to the toes.

The cushioning layer may be made of a deformable, resilient, or flexible material that is capable of absorbing shock. The materials may include polyurethane foam, neoprene, ethylene-vinyl-acetate (EVA), elastomer, nylon, etc. The cushioning layer may be a unitary piece molded from a single material, with varying thickness in regions, such as the fore area nearest the toes 108, the forefoot area 109, an arch area 110, and a heel area 102. Alternatively, the cushioning layer may be a multi-laminate constructed piece created from multiple layers of different types of materials. One method of creating the cushioning layer is to place a cover layer over an uncompressed foam material. The cover layer and uncompressed foam combination is then placed inside a mold and a compression molding technique is applied. For example, an example technique may be to place the uncompressed foam and cover layer combination into a heated cavity and applying heat and pressure to cure the uncompressed foam material.

The cushioning layer may be shaped or molded to curve on the sides 101 in order to conform to the shape of a foot. In particular, the medial side 105 may contain a raised portion that would lie underneath a portion of the medial arch region 106 of a foot. The curvature may be a result of the varying vertical thickness of the sides of the example adjustable orthotic or the particular angled curvature of the example adjustable orthotic itself. The heel area 102 may also have a heel cup and/or may alternatively project upward like the sides in order to prevent the foot from slipping. It is understood that dimensions and other values may vary depending on the number of models developed for various foot sizes.

The example embodiment of a cushioning layer may be of a homogenous consistency throughout the adjustable orthotic. For the comfort of the user, there would preferably not be bubbles in the foam large enough to be felt through a fabric surface, such as a polyester cover. For example, bubbles larger than 3 mm may be uncomfortable to some users. For the surface of the foam, more than 2 trapped bubbles per square inch or more than 6 surface bubbles with diameters outside the range of 1.5 mm to 3.0 mm may be unacceptable. Alternatively, the flexibility, hardness, thickness, resilience, or density of the example adjustable orthotic may vary throughout, either longitudinally, laterally, or vertically, e.g., by using a sandwich of multiple sub-layers in the cushioning layer, or by having a non-uniformly shaped mold.

The example embodiment of the cushioning layer for a woman's foot may be a polyurethane foam molded to the following specifications: a density in the range of 4.3 to 5.3 pounds per foot cubed; uncompressed foam forefoot thickness of 5.5 mm±1 mm; uncompressed foam heel thickness of 15.5 mm±1 mm; density of 4.3-5.3 lbs/ft$^3$; a tear strength of 5 lbs/in, and a compression set of 2.5%. The density of the cushioning layer may be 4.3 to 5.3 pounds per foot cubed (lbs/ft$^3$) or alternatively 70 to 88 kilograms per meter cubed (kg/m$^3$). The cushioning layer may weigh 12.0 grams ±3.0 grams, though the weight may be affected by the type of cover used. For example, a polyester cover may be used, having a weight of 240 g/yd$^2$±20 g/yd$^2$. The cushioning layer may have a hardness of 45-55 Shore OO, measured by placing the insole in a special jig and durometer measured on the fabric side with a mounted durometer gauge and recording the reading after 5 seconds. The example adjustable orthotic may vary in thickness along the various regions of the orthotic; however, the general thickness of the fore area near the toes 108 may be 1.5 mm±0.5 mm thick, the forefoot area 109 may be 2.5 mm±0.5 mm thick, the arch area 110 may be 3.6 mm±0.5 mm thick, and the heel region 102 may be 9.0 mm±1.0 mm thick. The length of the example embodiment may be 175 mm±5.0 mm from the distal 103 to proximal 104 end, and the width of the, example embodiment may be 81.0 mm±3.0 mm from the medial 105 to lateral 107 sides. It will be appreciated that lengths may be varied to provide multiple sizes.

The example embodiment of the cushioning layer for a man's foot may be a polyurethane foam molded to the following specifications: a density in the range of 4.3 to 5.3 pounds per foot cubed; uncompressed foam forefoot thickness of 5.5 mm±1 mm; uncompressed foam heel thickness of 15.5 mm±1 mm; density of 4.3-5.3 lbs/ft$^3$; a tear strength of 5 lbs/in, and a compression set of 2.5%. The density of the cushioning layer may be 4.3 to 5.3 pounds per foot cubed (lbs/ft$^3$) or alternatively 70 to 88 kilograms per meter cubed (kg/m$^3$). The cushioning layer may weigh 18.0 grams±3.0 grams, though the weight may be affected by the type of cover used. The cushioning layer may have a hardness of 40-50 Shore OO, measured by placing the insole in a special jig and durometer measured on the fabric side with a mounted durometer gauge, recording the reading after 5 seconds. The example adjustable orthotic may vary in thickness along the various regions of the orthotic; however, the general thickness of the fore area near the toes 108 may be 1.5 mm±0.5 mm thick, the forefoot area 109 may be 2.8 mm±0.5 mm thick, the arch area 110 may be 4.1 mm±0.5 mm thick, and the heel area 102 may be 10.0 mm±1.0 mm thick. The length of the example embodiment may be 194 mm±5.0 mm from the distal 103 to proximal 104 end, and the width of the example embodiment may be 94.0 mm±3.0 mm from the medial 105 to lateral 107 sides.

In order to provide greater comfort, or more traction, and/or to protect the cushioning layer from wear and tear, the adjustable orthotic may have a cover layer. The example embodiment has a cover made of 100% polyester situated above the cushioning layer. Alternative example embodiments of the adjustable orthotic may have a cover layer made from various types of materials, such as fabrics, leather, vinyl, polyurethane, latex, nylon, polyester blend, nylon blend, cotton, cotton blends, acrylic, any blend of the aforementioned materials, or any typical fabrics utilized in insole applications, etc. or any types of variants of these materials. The cover layer may be attached to the cushioning layer (or any intermittent layers) using a polyurethane adhesive. The shape and dimensions of the cover layer may conform to that of the cushioning layer. It is preferable that when placed on the cushioning layer, that the fabric not have wrinkles or at least wrinkles be less than or equal to 10 mm in length.

Figure 2:
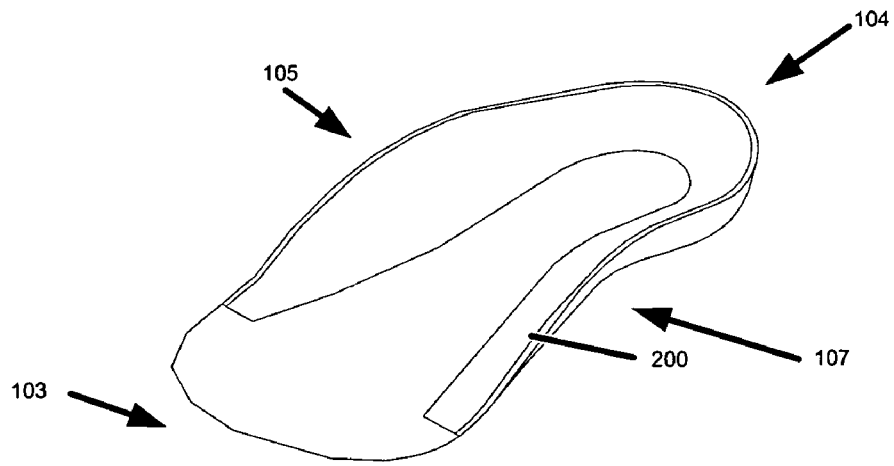
FIG. 2 illustrates an isometric view of an example adjustable orthotic, according to an example embodiment of the present invention.

FIG. 2 illustrates an isometric view of an example adjustable orthotic, according to an example embodiment of the present invention. Again, the distal 103, proximal 104, medial 105, and lateral 107 sides are indicated to provide the orientation. The thickness and angle of the curvature of the raised outer edge 200 of the example adjustable orthotic may vary depending on the mold or the laminating process. One method of constructing an adjustable orthotic would be to attach the cover layer, for example a cover made of 100% polyester, to a cushioning layer, for example a cushioning layer made of polyurethane foam. A shell layer, for example one made of thermoplastic urethane, may be attached to the underside of the cushioning layer using a polyurethane adhesive, or any other type of adhesive commonly used in insole applications. In alternative embodiments, intermittent secondary layers, which may have their own support functions, may be added to the bottom of the cushioning layer. The shell layer may then be attached to the underside of these secondary intermittent layers instead of to the cushioning layer.

Figure 3C:
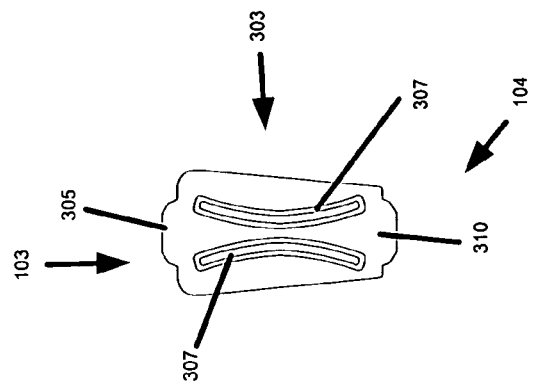
FIG. 3c illustrates the outside view of an example removable insert, according to an example embodiment of the present invention.
Figure 3B:
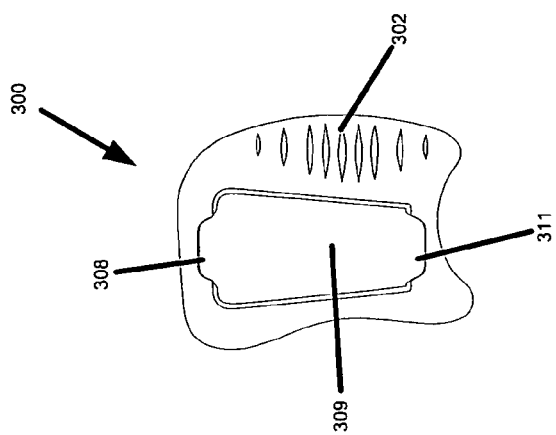
FIG. 3b illustrates a bottom view of an example shell layer of the adjustable orthotic of FIG. 3a, according to an example embodiment of the present invention.
Figure 3A:
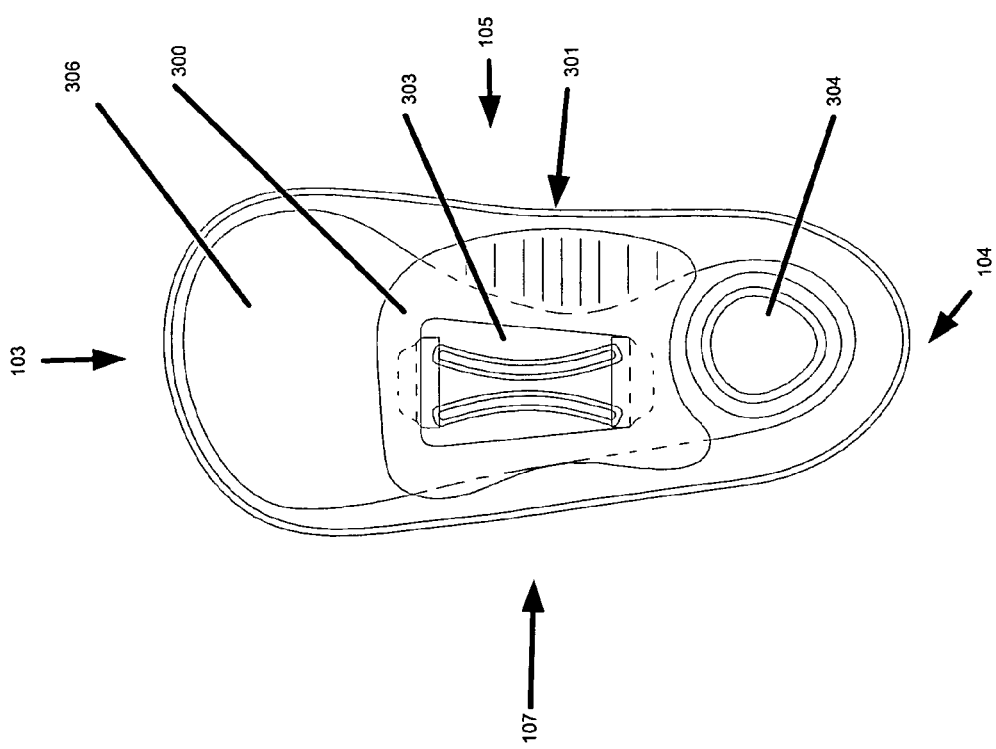
FIG. 3a illustrates a bottom view of an example adjustable orthotic with an insert, according to an example embodiment of the present invention.

FIG. 3a illustrates a bottom view of an example adjustable orthotic with an insert, according to an example embodiment of the present invention, and how the pieces of an adjustable orthotic may fit together. The bottom surface of the example adjustable orthotic faces the sole of the shoe when the example adjustable orthotic is properly positioned in a worn shoe. FIG. 3a contains an example adjustable orthotic that would receive the right foot. The distal 103, proximal 104, medial 105, and lateral 107 sides are shown again to provide orientation. The bottom of the cushioning layer 306 may contain a deformable depression 304 in the heel region. The deformable depression 304 is shaped to distribute the weight of impact from a user's foot. In alternative embodiments, the deformable depression 304 may be located on the top area of the cushion or even in other parts of the orthotic that are likely to receive particularly high impact forces from a user's foot.

A shell layer 300 extends along a portion of the bottom of the orthotic. The shell layer 300 may be configured to extend longitudinally from at least the talus-navicular joint to the medial cuneiform-first metatarsal joint and laterally under at least the medial cuneiform bone to support the arch cavity when the orthotic is in use. In the example embodiment illustrated, the shell layer longitudinally extends across at least a portion of the arch cavity and over a part of the medial arch region 301 and laterally extends beneath so as to support the arch cavity of the foot. While the shell layer 300 may extend the entire range of the foot, it need not extend through the entire foot. For example, the shell layer, as shown in the figure, may extend below just the middle region of the foot, in particular a part of the medial arch region 301 or under a part of the arch cavity. Variations in length may vary depending on the type of hardness and stiffness of the shell material, the shape of the shell layer and type of support provided by the shell, the shape of the insert and the type of configuration used to receive a removable insert, the cost of the material, etc. The shell layer 300 supports the arch cavity, with support and comfort added by the cushioning layer. Alternative embodiments of the orthotic may have the cushioning layer 306 longitudinally extend beyond the posterior and/or the anterior ends of the shell layer 300. The example embodiment of the shell layer may be attached to the cushioning layer with a polyurethane adhesive and preferably may not have gaps between the shell layer and the cushioning more than 0.5 mm.

A removable insert 303 is received by the shell layer 300 in the insert receiving location area 309 of the shell layer 300, e.g. a cavity, divot or depression shaped to receive a particular insert. The receiving location may be shaped so that it conforms to or contains the insert 303, when the insert 303 is inserted. In the example illustrated, the insert 303 when received may be completely within the convex hull of the receiving location. Alternatively, it will be appreciated that the insert 303 may be attached or protrude outside the convex hull in the region of the arch cavity. The removable insert may include protruding ribs 307 that are shaped to curve away from each other. The protruding ribs 307 may provide additional structural stability to the insert and orthotic. The protruding ribs 307 may take on a variety of shapes, sizes, and geometries. The protruding ribs 307 extend longitudinally along the body of the removable insert. A distal insert tab 305 and proximal insert tab 310 on the longitudinal ends of the insert allow the insert to be attached to the example shell layer of an example adjustable orthotic by inserting the distal insert tab 305 and proximal insert tab 310 through a distal aperture 308 and proximal aperture 311, respectively.

FIG. 3b illustrates a bottom view of an example shell layer of the adjustable orthotic of FIG. 3a, according to an example embodiment of the present invention. The shell layer may be configured to receive a removable insert 303 that alters the amount of support provided by the orthotic. In one embodiment, the insert receiving location may be a generally rectangular opening 309 on a bottom surface of the shell layer 300 which extends longitudinally from at least the talus-navicular joint to the medial cuneiform-first metatarsal joint when the orthotic is in use, the opening configured to receive the removable insert. The opening 309 is generally located in the center of the shell layer, although the location may be altered. The opening 309 includes a distal aperture 308 and proximal aperture 311, in this example embodiment located at the longitudinal ends, extending through the shell layer. The apertures 308 and 311 may be configured to receive insertion tabs 305 and 310, respectively, unitarily molded on the removable insert. It will be appreciated that the size and location of the opening 309 may be varied. It will further be appreciated that alternative approaches to attach and/or retain the insert in the proper position may be employed, e.g. via a clip, hook and loop fabric, friction fit, a pin and hole assembly, clasp, etc.

The portion of the medial arch region 301 of the example shell layer 300 may also contain protruding ribs or ridges 302. These ribs/ridges 302 may provide traction and stability in the medial arch region. Moreover, the ridges 302 may provide additional structural stability with less material and better moldability. The ribs/ridges 302 may also come in a variety of shapes, sizes, and geometries. Alternatively, a portion of the medial arch region 301 of the shell layer 300 may instead contain generally oval shaped holes, or the shell layer 300 may contain a combination of ridges and holes. Like that of the protruding ridges, these holes may provide traction and stability in the medial arch region.

FIG. 3c illustrates the outside view of an example removable insert 303, according to an example embodiment of the present invention. The view being shown is the side of the example removable insert that would be touching the sole of the shoe when placed inside of the shoe. The distal 103 and proximal 104 ends of the example removable insert correspond longitudinally with that of the example adjustable orthotic of FIG. 3a. While in this example, the proximal 104 end is narrower than that of the distal 103 end, it will be appreciated that the insert may be molded into various shapes depending on the type and level of support. This is similarly true for the shape of the opening 309 of the insert receiving location of the shell layer 300.

Figure 4:
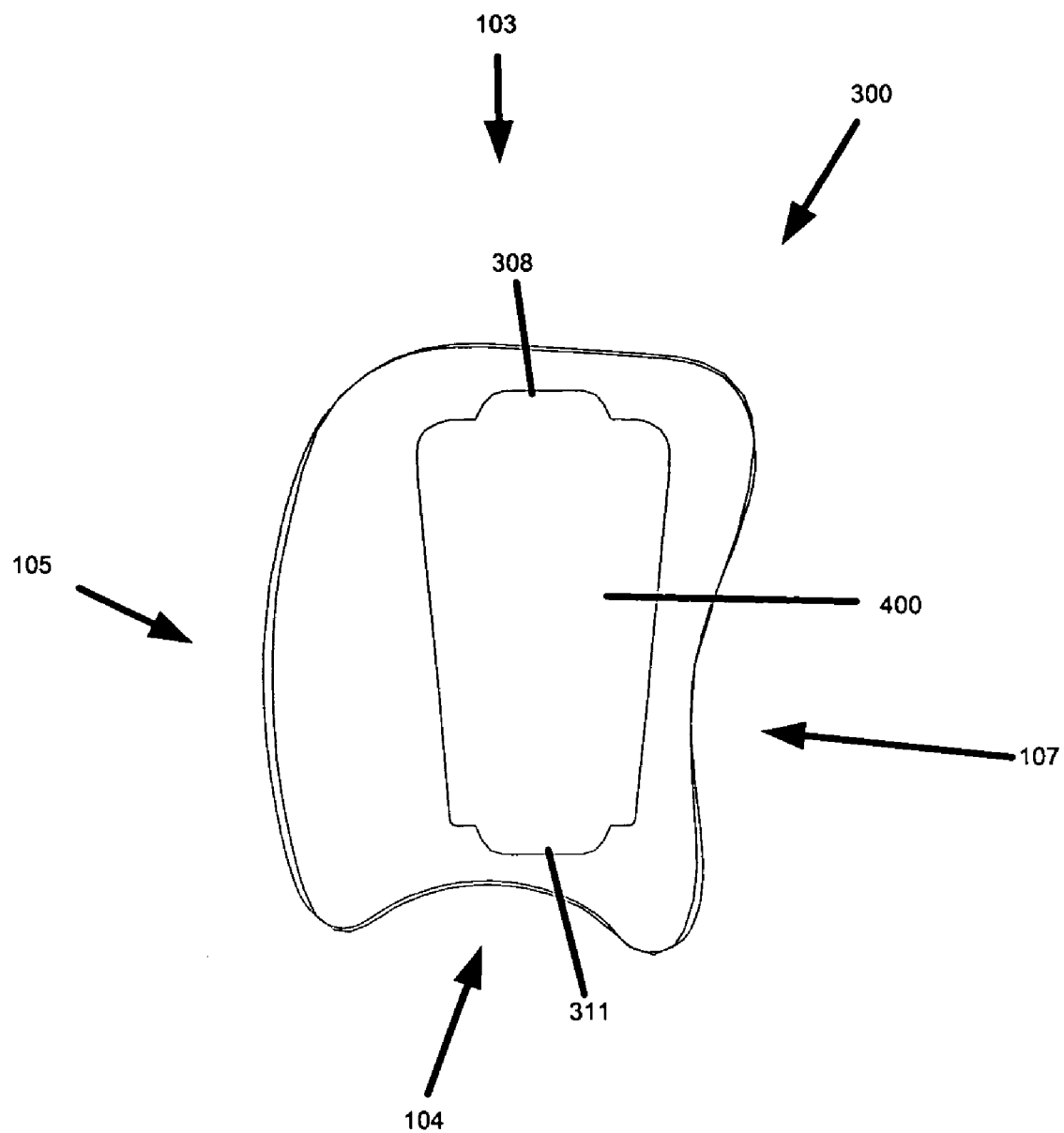
FIG. 4 illustrates a top view of the shell layer of the example embodiment of the adjustable orthotic of FIG. 3a, according to an example embodiment of the present invention.

FIG. 4 illustrates a top view of the shell layer 300 of an example embodiment of an adjustable orthotic. The top portion of the shell layer would be adjacent to that of the cushioning layer 306. For purposes of orientation, the distal 103, proximal 104, medial 105, and lateral 107 sides are indicated. In the example embodiment that contains an opening in the insert receiving location, the opening 400 would be protruding out of the top of the shell layer 300 into the cushioning layer 306. Moreover, the apertures 308 and 311 to receive an insert 303 may extend through the shell layer 300. Alternatively, the apertures may be molded as cavities, dents or divots that do not extend all the way through the shell layer, which may receive the insert tabs.

The hardness of a material in an orthotic may be measured on the Shore Hardness scale by a durometer. The hardness measures the resistance of plastics toward indentation. The Shore A scale is for softer rubbers while the Shore D scale is for harder rubbers or plastics. Moreover, because indentation readings may change over time, the indentation time is sometimes provided or else a range is provided for the hardness level. Furthermore, different scales may be used to test or define different levels of hardness, but a hardness on one scale may still be equivalent to a different value on another scale. For example, a Durometer A hardness range of approximately 70 to 95 may overlap with the Durometer D hardness range of approximately 30 to 60. Moreover, it is understood that measurements using a different measurement method may still fall within specified ranges measured under a Shore Hardness scale.

The shell layer material is preferably thermoplastic urethane (TPU) with a shore hardness of 95A. The shell layer may also be made from polyolefins, polyamides, polyurethanes, acrylonitrile-butadiene-styrene (ABS), styrene-ethylene-butylene-styrene (SEBS), and other materials utilized in insole applications. The shell layer may range in hardness from 90A to 100A or at least below 59D to 64D.

The example embodiment of the shell layer of an adjustable orthotic for a woman's foot may have a thickness of 1.2 mm±0.12 mm. The length of the shell layer of the example embodiment may be 78.8 mm±2 mm from the longest points from the distal 103 to proximal 104 end, and the width of the shell layer example embodiment may be 63.4 mm±2 mm from the widest points of the medial 105 to lateral 107 sides.

The example embodiment of the shell layer of an adjustable orthotic for a man's foot may have a thickness of 1.3 mm±0.12 mm. The length of the shell layer of the example embodiment may be 87.2 mm±2 mm from the longest points from the distal 103 to proximal 104 end, and the width of the shell layer example embodiment may be 73.1 mm±2 mm from the widest points of the medial 105 to lateral 107 sides.

Figure 5:
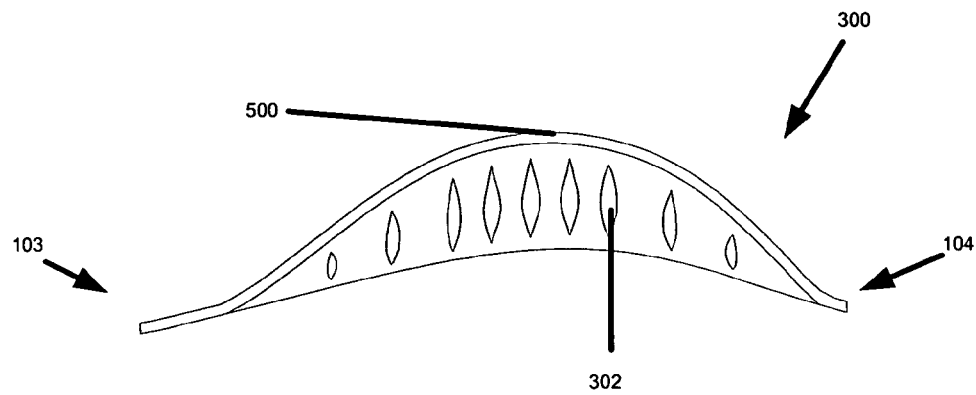
FIG. 5 illustrates a medial side view of the shell layer of the example adjustable orthotic of FIG. 3a, according to an example embodiment of the present invention.

FIG. 5 illustrates a medial side view of the shell layer 300 of the example adjustable orthotic of FIG. 3a, according to an example embodiment of the present invention. The distal end 103 is on the left and the proximal end 104 is on the right. The edge of the orthotic may extend laterally up the side of the medial arch. The end of the medial edge of the arch 500 may extend up along the side of the foot to the peak of the medial arch. However, alternative embodiments may have the medial edge only extend halfway up the peak of the medial arch. Generally protruding ribs 302 may line the arch region, but alternatively, the arch region may contain holes, have a plain surface, or be molded with a different pattern.

Figure 6:
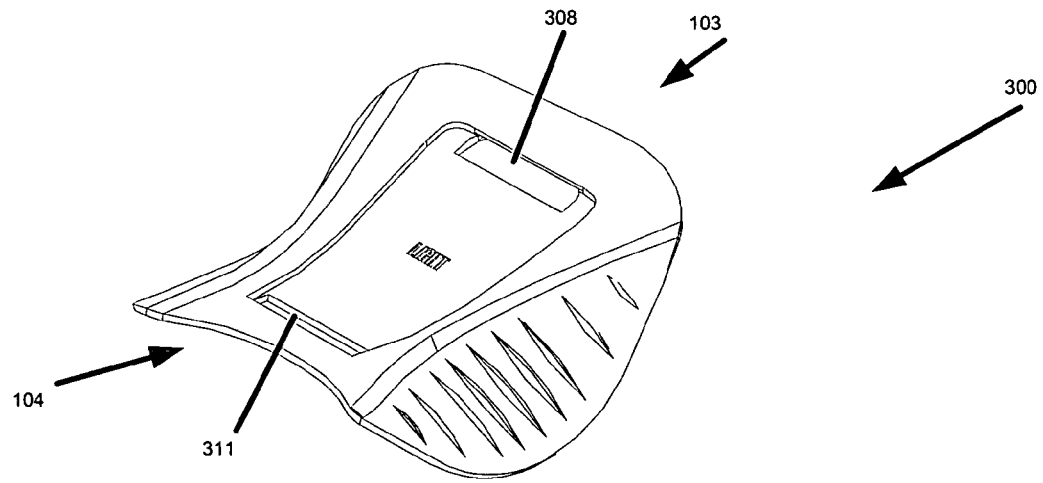
FIG. 6 illustrates an isometric view of the shell layer of the example adjustable orthotic of FIG. 3a, according to an example embodiment of the present invention.

FIG. 6 illustrates an isometric view of the shell layer 300 of the example adjustable orthotic, according to an example embodiment of the present invention. The distal end 103 and proximal 104 ends are shown for purposes of orientation. This provides another view of the apertures 308 and 311 configured to receive insertion tabs 305 and 310, respectively, of a removable insert. In the example shown, the apertures extend all the way through the shell layer. It will be appreciated they need not do so in alternative embodiments.

Figure 7:
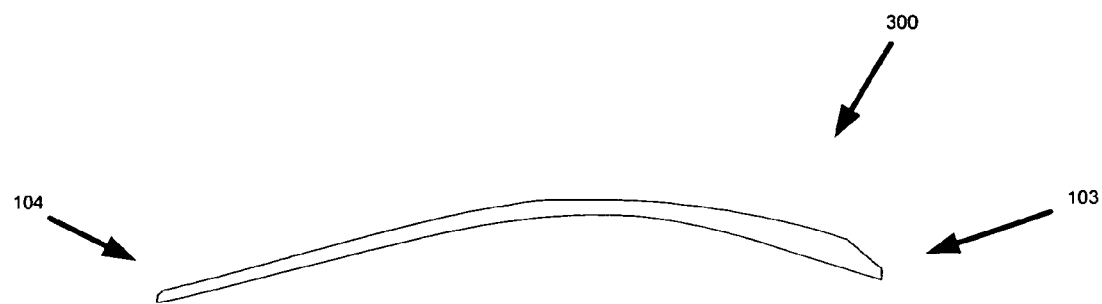
FIG. 7 illustrates a lateral side view of the example adjustable orthotic shell layer of FIG. 5, according to an example embodiment of the present invention.

FIG. 7 illustrates a lateral side view of the example adjustable orthotic shell layer 300, according to an example embodiment of the present invention. The distal end 103 and proximal 104 ends are shown for purposes of orientation. The shell layer may be a unitary piece that is molded from materials that are harder and stiffer than the cushioning layer. The lateral longitudinal arch may not be as pronounced as the medial longitudinal arch, thus the lateral arch height may be relatively shorter. The shape of the shell layer may curve like that of the middle of a foot, providing both comfort and support to the arch cavity.

Figure 8:
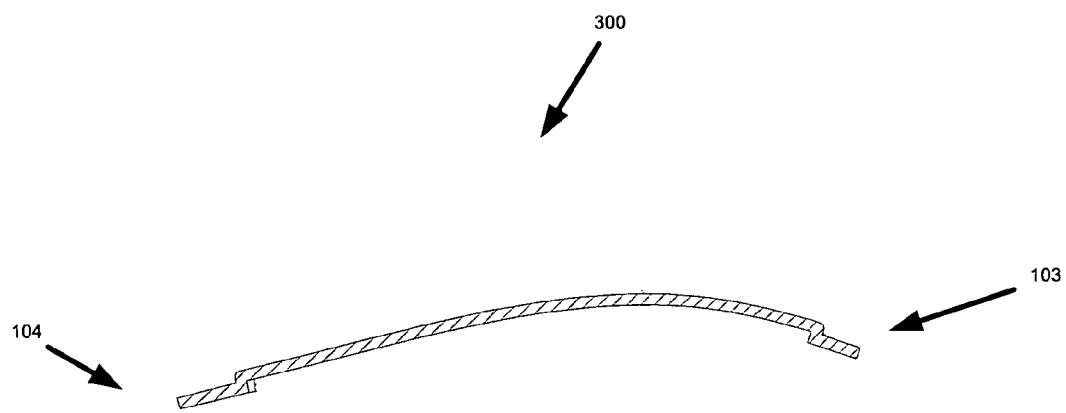
FIG. 8 illustrates a mid-line cross-section side view of the example adjustable orthotic shell layer of FIG. 5, according to an example embodiment of the present invention.

FIG. 8 illustrates a mid-sagittal planar view of an example adjustable orthotic shell layer 300, according to an example embodiment of the present invention. The distal end 103 and proximal 104 ends are shown for purposes of orientation. The cross-section illustrates the material, such as thermoplastic urethane (TPU), which may be homogeneous in material and equally hard and stiff across the shell layer when molded. Moreover, the thickness is relatively constant longitudinally throughout the shell layer. The shell may be created using conventional manufacturing processes, e.g., injection molding of chemicals, such as thermoplastic urethane.

The shell layer itself has a hardness and stiffness that can provide comfort and support to a user. If the user wants light support, the orthotic may be worn without an insert, i.e. placed inside a shoe without a removable insert received within the orthotic. The word "light" may be written on the outside of the shell to indicate to a user that the shell itself may provide the first and lightest level of support. Inserts may be inserted to alter the comfort and support properties of the shell layer.

Figure 9:
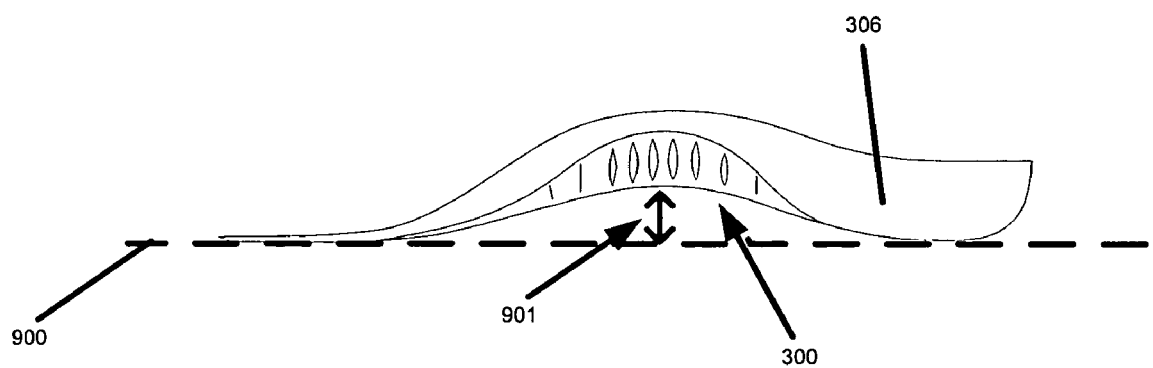
FIG. 9 illustrates a medial side view of the example adjustable orthotic of FIG. 3a, according to an example embodiment of the present invention.

FIG. 9 illustrates a medial side view of the example adjustable orthotic of FIG. 3a, according to an example embodiment of the present invention. A dotted line 900, representing a horizontal plane, is provided for context to view the curvature of the arch. The arch clearance 901 of the curve of an example shell layer 300 can be seen to substantially conform with that of the cushioning layer 306. The example embodiment of an adjustable orthotic for a woman's foot may have an arch clearance 901 of 12.0 mm±2.0 mm. The example embodiment of an adjustable orthotic for a man's foot may have an arch clearance 901 of 13.5 mm±2.0 mm.

Figure 10:
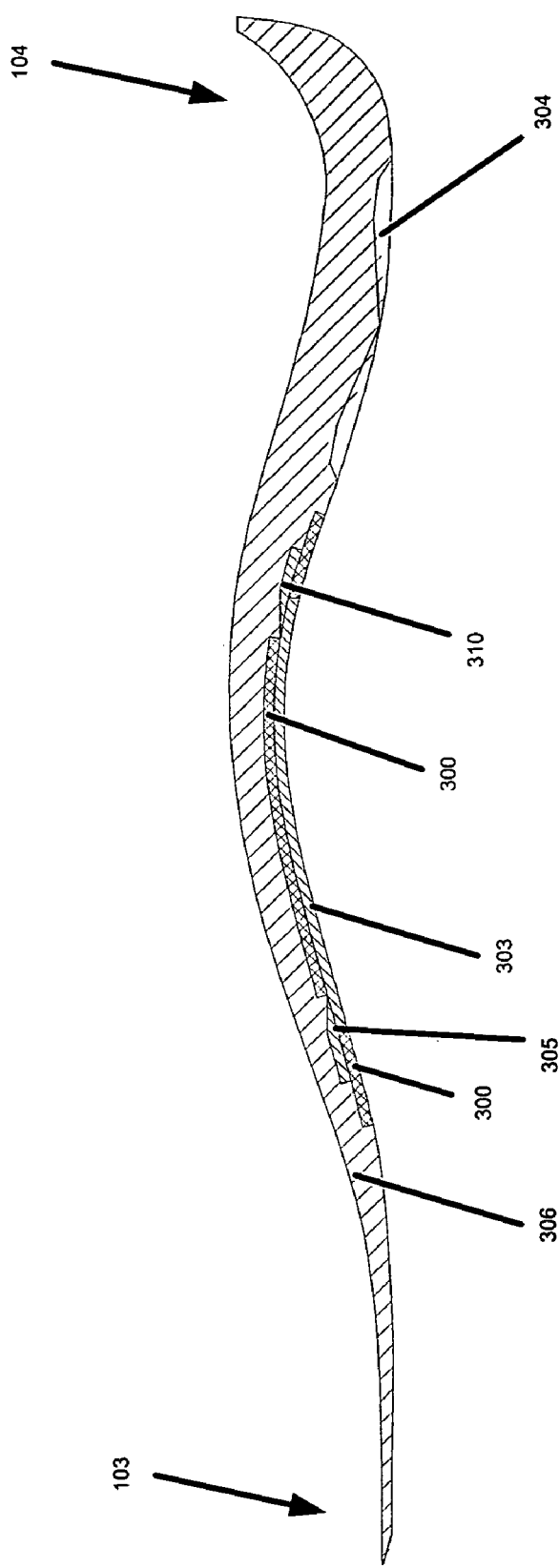
FIG. 10 illustrates a mid-sagittal planar view of the example adjustable orthotic of FIG. 3a, according to an example embodiment of the present invention.

FIG. 10 illustrates a mid-sagittal planar view of the example adjustable orthotic of FIG. 3a, according to an example embodiment of the present invention. The distal 103 and proximal 104 ends of the example adjustable orthotic are shown to provide orientation. The shell layer 300 attaches to the bottom of the cushioning layer 306. In the illustrated embodiment, both the shell layer 300 and the cushioning layer 306 conform to each other laterally and longitudinally. Moreover, in this example, the cushioning layer may be a unitary piece with a homogenous density. It is appreciated that the density and/or thickness of a cushioning layer may also be heterogeneously formed, such as through a molding process, layering process using layers of different densities, etc. The heel area in the proximal end shows the depth of the deformable depression 304. Moreover, the view also illustrates the interconnectedness between the removable insert 303 and the shell layer 300. The tabs 305 and 310 of the removable insert 303 extend through the shell layer 300 and into the cushioning layer 306 on both ends of the shell layer. The tabs 305 and 310 extend through apertures 308 and 311, respectively, which cannot be viewed from this angle but are shown in FIG. 6.

Figure 11:
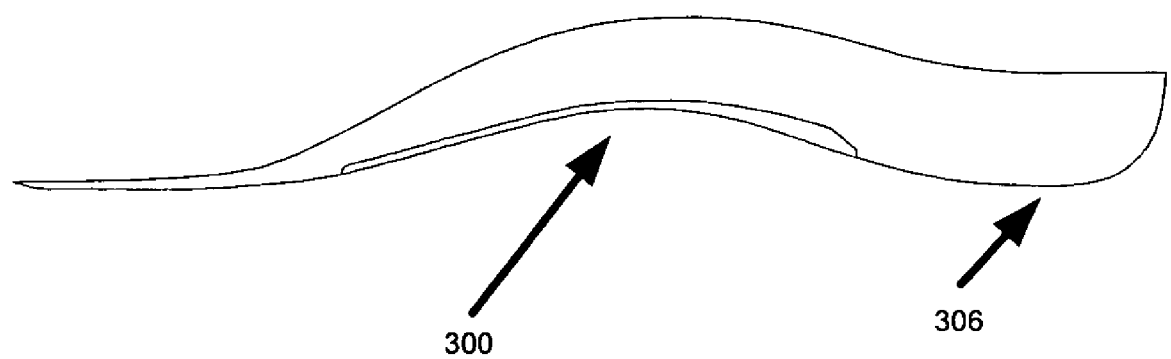
FIG. 11 illustrates a lateral cross-section view of the example adjustable orthotic of FIG. 3a, according to an example embodiment of the present invention.

FIG. 11 illustrates a lateral cross-section view of the example adjustable orthotic of FIG. 3a, according to an example embodiment of the present invention. Unlike on the medial side, the shell layer 300 does not extend up as far on the lateral side of the cushioning layer 306. It will be appreciated that alternative designs may be used, e.g. a shell layer configured to provide support for supination rather than pronation may extend along the lateral edge of the foot. In an alternative shell layer configured to support supination, an insert may be received on the edge of a lateral longitudinal arch of an orthotic rather than in the edge portion of a medial longitudinal arch region configured to provide support for pronation.

Figure 12:
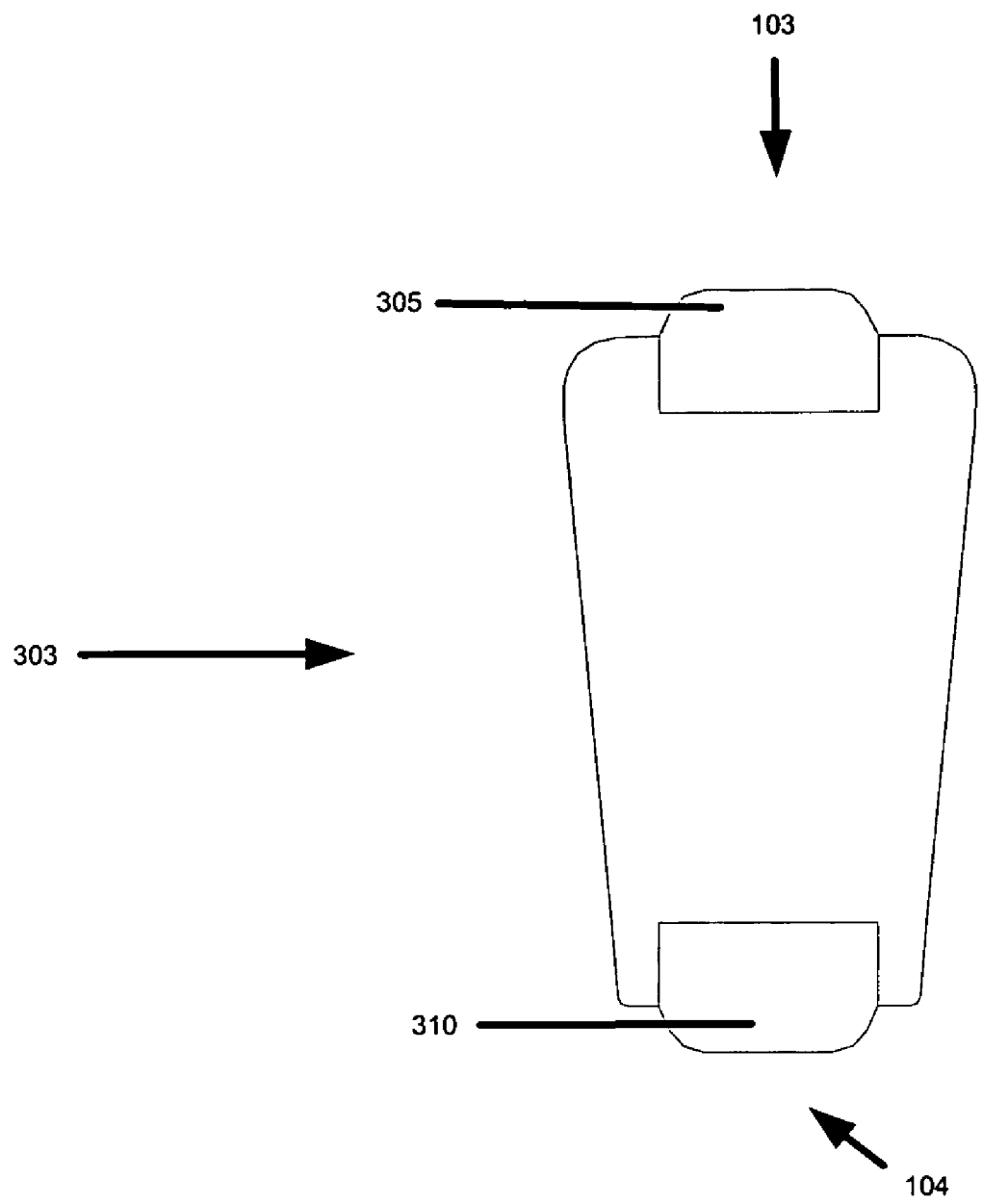
FIG. 12 illustrates the top/inside view of the example removable insert of FIG. 3c, according to an example embodiment of the present invention.

FIG. 12 illustrates the top/inside view of the example removable insert 303, according to an example embodiment of the present invention. The distal tab 305 and proximal tab 310 extend out of the body which will be seen more clearly in FIG. 13. The tabs may be unitarily molded as part of the body. A set of inserts may be provided of increasing stiffness and/or hardness. Each successively stiffer insert may provide a greater degree of support. Alternatively, inserts may have different dimensions, e.g. length, so that when inserted they alter the shape and support properties of the adjustable orthotic. The inserts are generally of the thickness of the shell layer if they are inserted into an opening; however, removable inserts that are attached to the outside of the shell, or which bulge out away from the shell, may be of greater thickness. One insert set may be made of thermoplastic urethane (TPU) of a hardness shore 64D. A second, firmer insert set may be made of a mixture of 65% injection-molded TPU of a hardness shore 64D and 35% acrylonitrile-butadiene-styrene (ABS) to create a molded removable insert with hardness shore 74D.

In the example embodiment, the removable insert may have similar dimensions to the shell layer opening that was configured to receive the removable insert.

For example, the example embodiment of the medium and firm removable inserts of an adjustable orthotic for a woman's foot may, in conformance with the opening 309 in the shell layer 300, have a thickness of 1.2 mm±0.12 mm. The length of the removable inserts of the example embodiment may be 60.5 mm±2 mm from the distal 103 to proximal 104 ends, including the length of the tabs. The width of the removable inserts of the example embodiment may be 30.0 mm±2 mm at the distal end 103 and may vary in narrowness at the proximal end 104, depending on the angle of the trapezoidal edges.

The example embodiment of the medium and firm removable inserts of an adjustable orthotic for a man's foot may have a thickness of 1.3 mm±0.12 mm. The length of the removable inserts of the example embodiment may be 66.9 mm±2 mm from the distal 103 to proximal 104 end, including the length of the tabs. The width of the removable inserts of the example embodiment may be 34.6 mm±2 mm at the distal end 103 and may vary in narrowness at the proximal end 104, depending on the angle of the trapezoidal edges.

Figure 13:
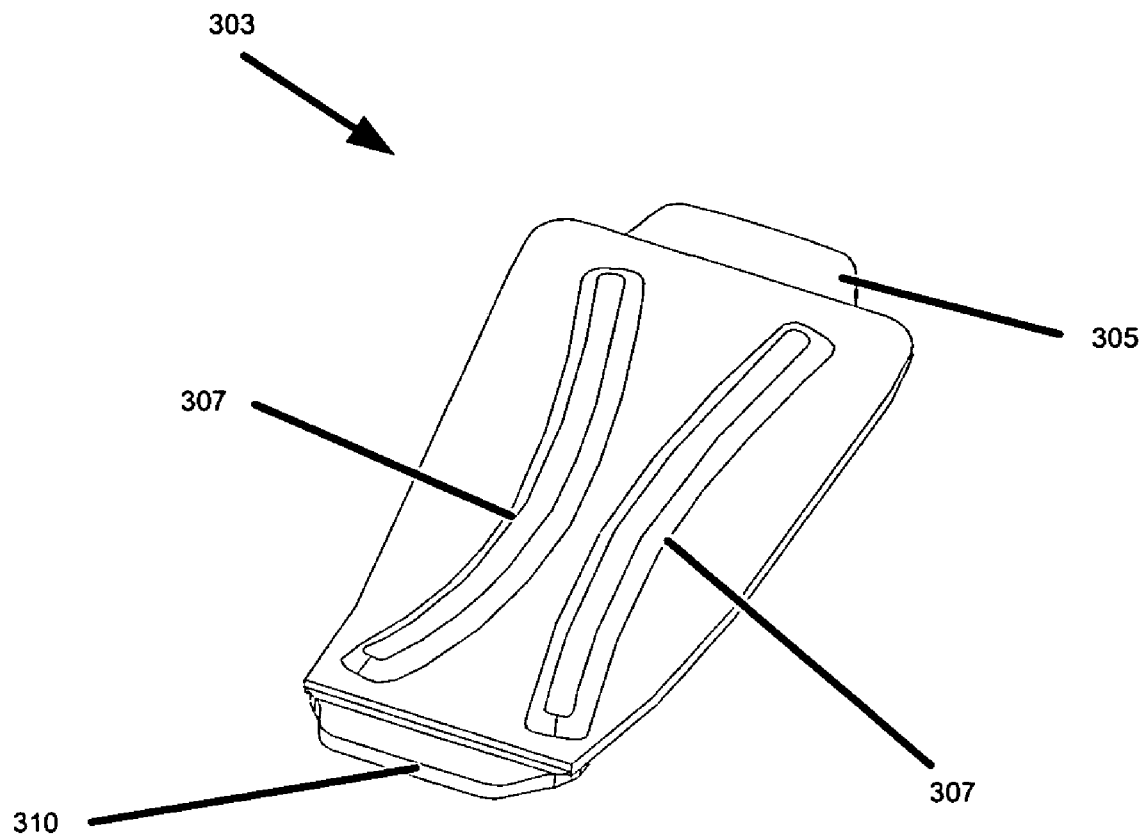
FIG. 13 illustrates an isometric view of the example removable insert of FIG. 3c, according to an example embodiment of the present invention.

FIG. 13 illustrates an isometric view of the example removable insert 303, according to an example embodiment of the present invention. Protruding ribs 307 may be integrally molded as part of the insert. The ribs 307 may provide support and/or stiffen the insert. A proximal insert tab 310 and distal insert tab 305 may extend out from the longitudinal ends of the insert.

Figure 14:
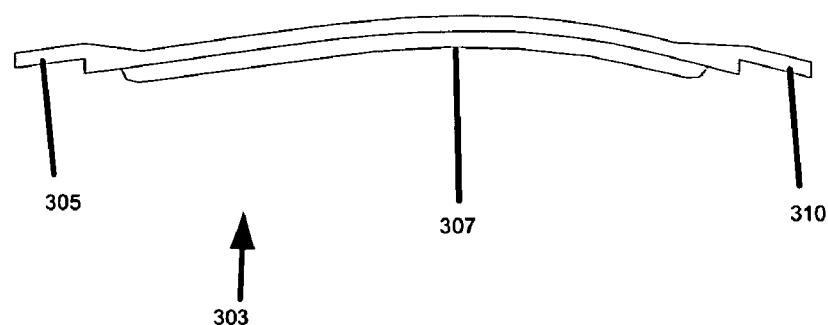
FIG. 14 illustrates a medial view of the example removable insert of FIG. 3c, according to an example embodiment of the present invention.
Figure 15:
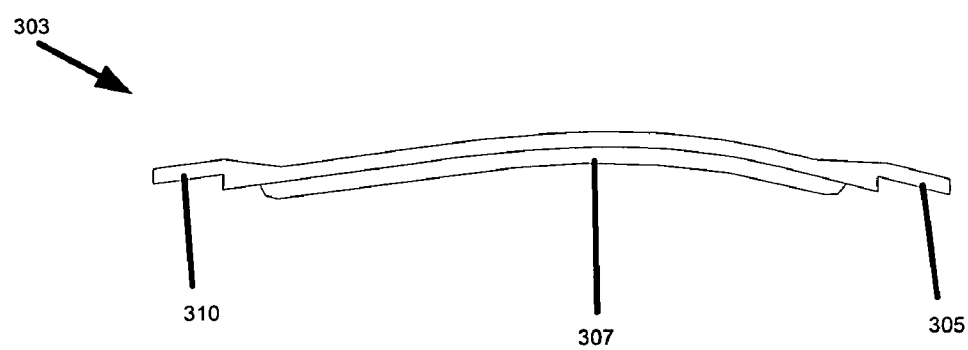
FIG. 15 illustrates a lateral view of the example removable insert of FIG. 3c, according to an example embodiment of the present invention.

FIG. 14 illustrates a medial view of the example removable insert 303, according to an example embodiment of the present invention. FIG. 15 illustrates a lateral view of the example removable insert 303, according to an example embodiment of the present invention. The example removable insert is symmetric along its longitudinal axis. It will be appreciated that alternative asymmetric designs may also be used. The protruding ribs 307 are illustrated at the bottom of both FIGS. 14 and 15, and the distal insert tab 305 and proximal insert tab 310 may be seen to jut out from the ends of the insert. The medial view also shows the curvature of the insert, which when inserted conforms to the shape and curvature of the shell layer. However, it is appreciated that the insert may curve differently than the shell layer and cushioning layer to provide alternative levels of support and/or stiffness.

Figure 16:
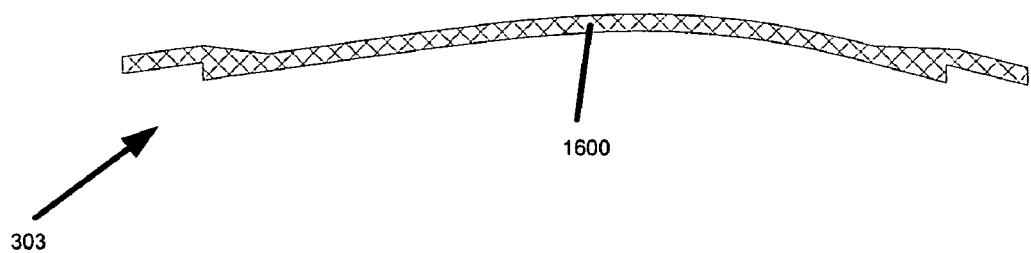
FIG. 16 illustrates a mid-sagittal planar view of the example removable insert of FIG. 3c, according to an example embodiment of the present invention.

FIG. 16 illustrates a mid-sagittal planar view of the example removable insert 303, according to an example embodiment of the present invention. The inside 1600 of the insert is a generally homogeneous material of relatively constant thickness and density. However, it is appreciated that alternative embodiments of a removable insert may be of heterogeneous density and/or thickness. In the example adjustable orthotic the shell layer provides light support. In the example orthotic, the inserts are harder than the shell layer itself. The inserts are dimensionally similar to each other, but have different material properties. For example, if a user wanted "medium" support, an insert may be attached to the shell layer, the insert being made from thermoplastic urethane of a shore hardness of 59D to 69D. If a user wanted "firm" support, a harder insert may be attached, the insert being made from a combination of 65% thermoplastic urethane (TPU) of shore hardness 64D and 35% acrylonitrile-butadiene-styrene (ABS), with a total shore hardness of 69D to 79D. The percentage of TPU may vary between 60 to 70% and the percentage of ABS may vary from 30 to 40%, variations of which could alter both the hardness and stiffness of the insert. In other words, the ratio of TPU to ABS could range from a high of 7/3 to a low of 3/2. Alternatively, dimensionally different inserts may provide different levels of support.

Although inserts in the illustrated examples are molded from a uniform composition, alternatives need not be uniform, e.g. laminates and/or multi-piece assemblies may be used.

Figure 17:
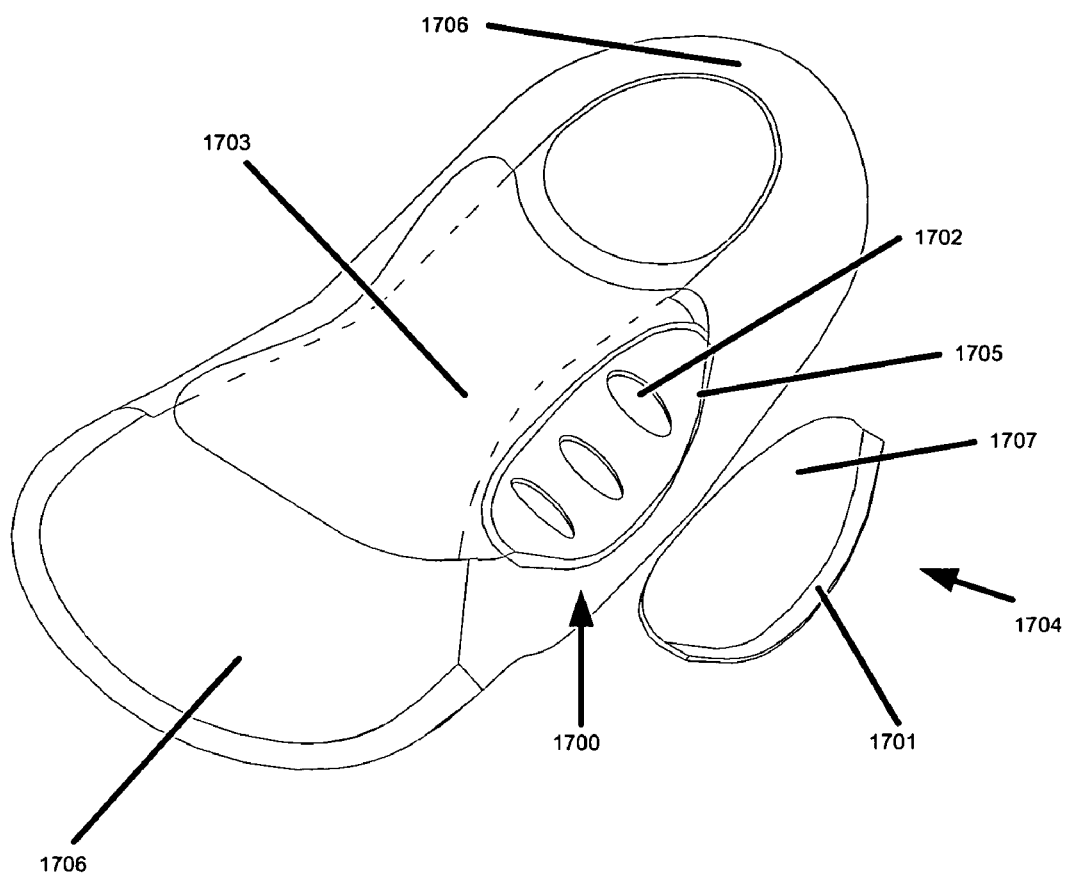
FIG. 17 illustrates an isometric view of the bottom of an alternative example adjustable orthotic and insert.

One alternative example adjustable orthotic allows inserts to be inserted on the medial side of the shell layer rather than on the bottom. FIG. 17 illustrates an isometric view of the bottom of an alternative example adjustable orthotic and insert, according to an example embodiment of the present invention. The alternative example has a shell layer 1703 configured to receive a removable insert 1704 for side-insertion between an edge portion of the medial arch region 1700 of the shell layer and the cushioning layer 1706. The shell layer area configured to receive a removable insert 1704 that alters an amount of support provided by the orthotic may be located in a part of the medial arch region 1700 of the shell layer. The shell layer 1703 and inserts 1704 may provide adjustable arch support for the arch cavity by adjusting the edge portion of the medial arch region 1700.

The edge of the medial arch region 1700 may contain a space 1705 between the shell layer 1703 and the cushioning layer 1706 (or any intermittent secondary layers) configured to receive a removable insert 1704 which adjusts the amount of arch support provided by the orthotic. The removable insert 1704 may contain a lip 1701 that extends at a different angle than the section 1707 of the removable insert that would fit into the edge portion of the medial arch region 1700. To ensure a tight fit, the space 1705 between the shell layer 1703 and cushioning layer 1706 may be of approximately the same thickness as the section 1707 of the received removable insert 1704. Moreover, the shape of the section 1707 that is actually within the space 1705 between the layers conforms substantially to the shape of the curve of the edge portion of the medial arch region 1700. When the removable insert 1704 is placed between the shell layer 1703 and cushioning layer 1706, the lip 1701 protrudes out in order to provide easier access to remove the insert.

Moreover, in FIG. 17, the bottom, center of the orthotic would not contain an opening, like in the example embodiment of FIG. 3b. This area could contain circular concave grooves, oval-shaped holes (similar to those found in the arch region), protruding ribs, or other adjustments to the bottom of the shell surface that could provide further support or further traction between the shell layer and the inside of a user's shoe. Moreover, the edge portion of the medial arch region 1700 may also contain oval-shaped holes 1702, or possibly protruding ribs or other adjustments in the shell layer.

Figure 18:
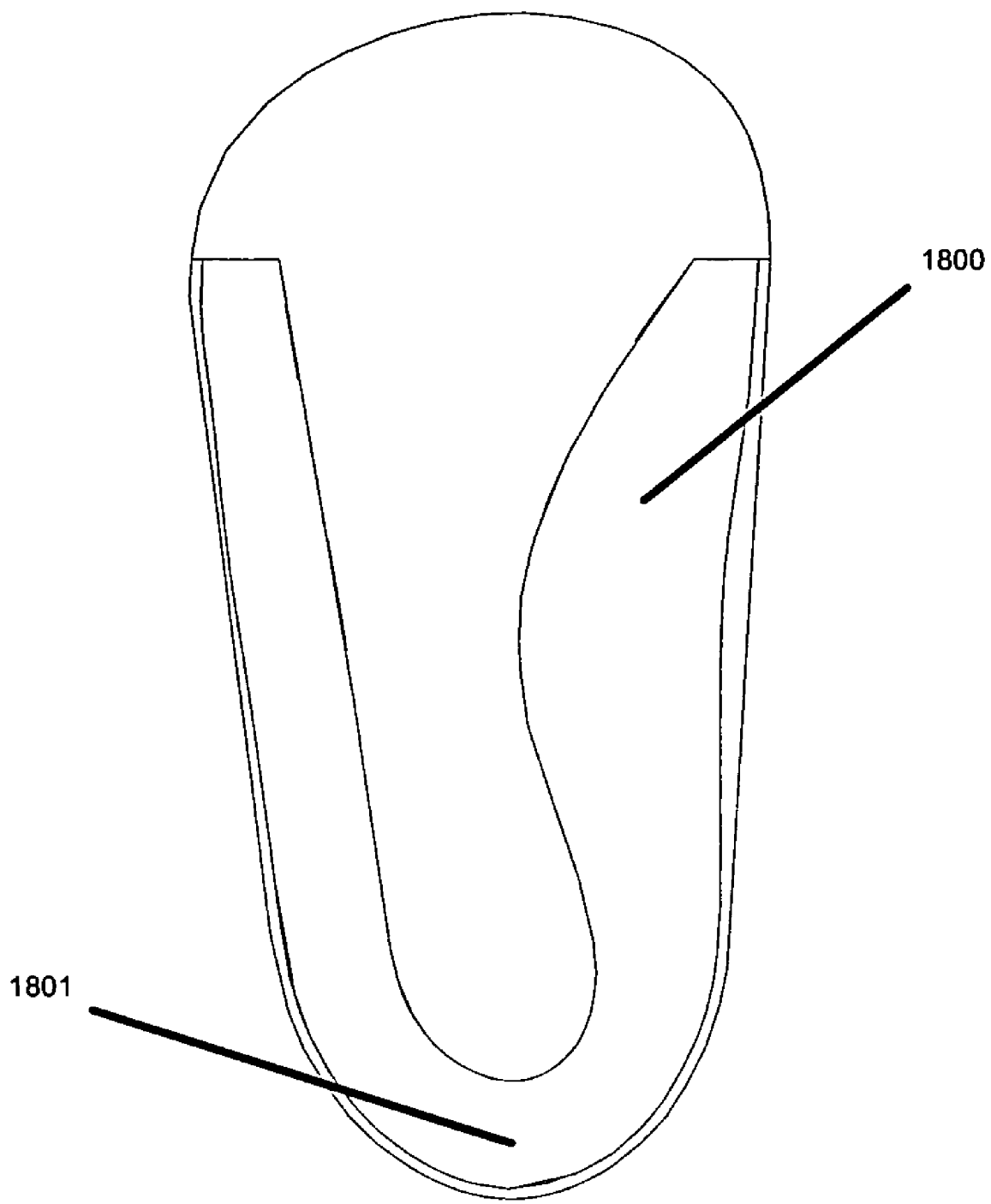
FIG. 18 illustrates a top view of the alternative example adjustable orthotic of FIG. 17, according to an example embodiment of the present invention.

FIG. 18 illustrates a top view of the alternative example adjustable orthotic of FIG. 17, according to an example embodiment of the present invention. The top view of FIG. 18 may be similar to the top of the example illustrated in FIG. 1. For example, the sides 101 of FIG. 1 may be similar to the sides 1800 illustrated in FIG. 18, and may similarly contain raised portions. The heel area 102 of FIG. 1 may be similar to the heel area 1801 of FIG. 18. Like the heel area 102 of FIG. 1, the heel area of FIG. 18 may also have a heel cup and/or may alternatively project upward like that of the sides in order to prevent the foot from slipping around.

Figure 19:
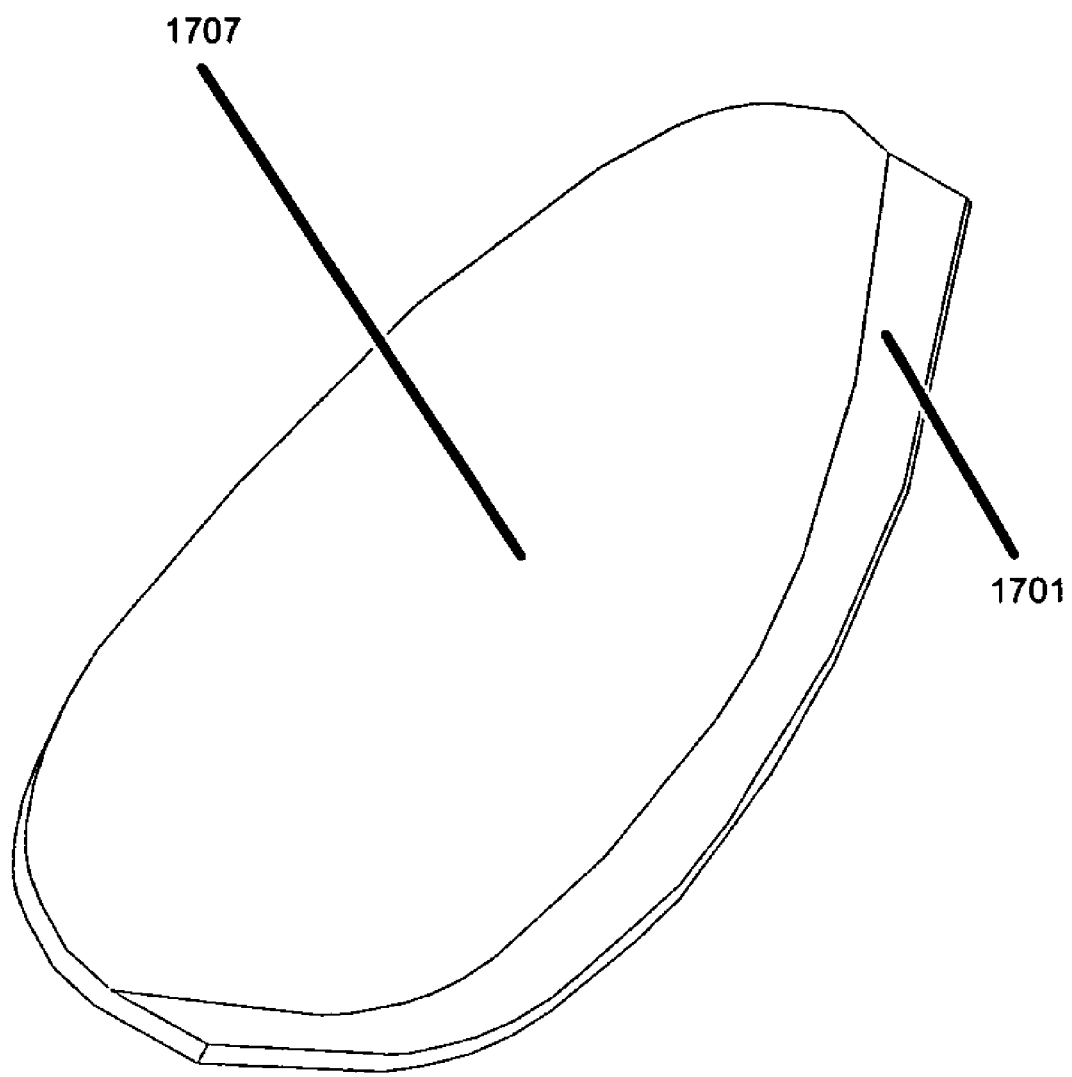
FIG. 19 illustrates an isometric view of the alternative example adjustable orthotic insert of FIG. 17, according to an example embodiment of the present invention.

FIG. 19 illustrates an isometric view of the alternative example adjustable orthotic insert of FIG. 17, according to an example embodiment of the present invention. The lip 1701 may be at a different angle than that of the section 1707 of the insert that is actually received inside the orthotic.

Figure 20:
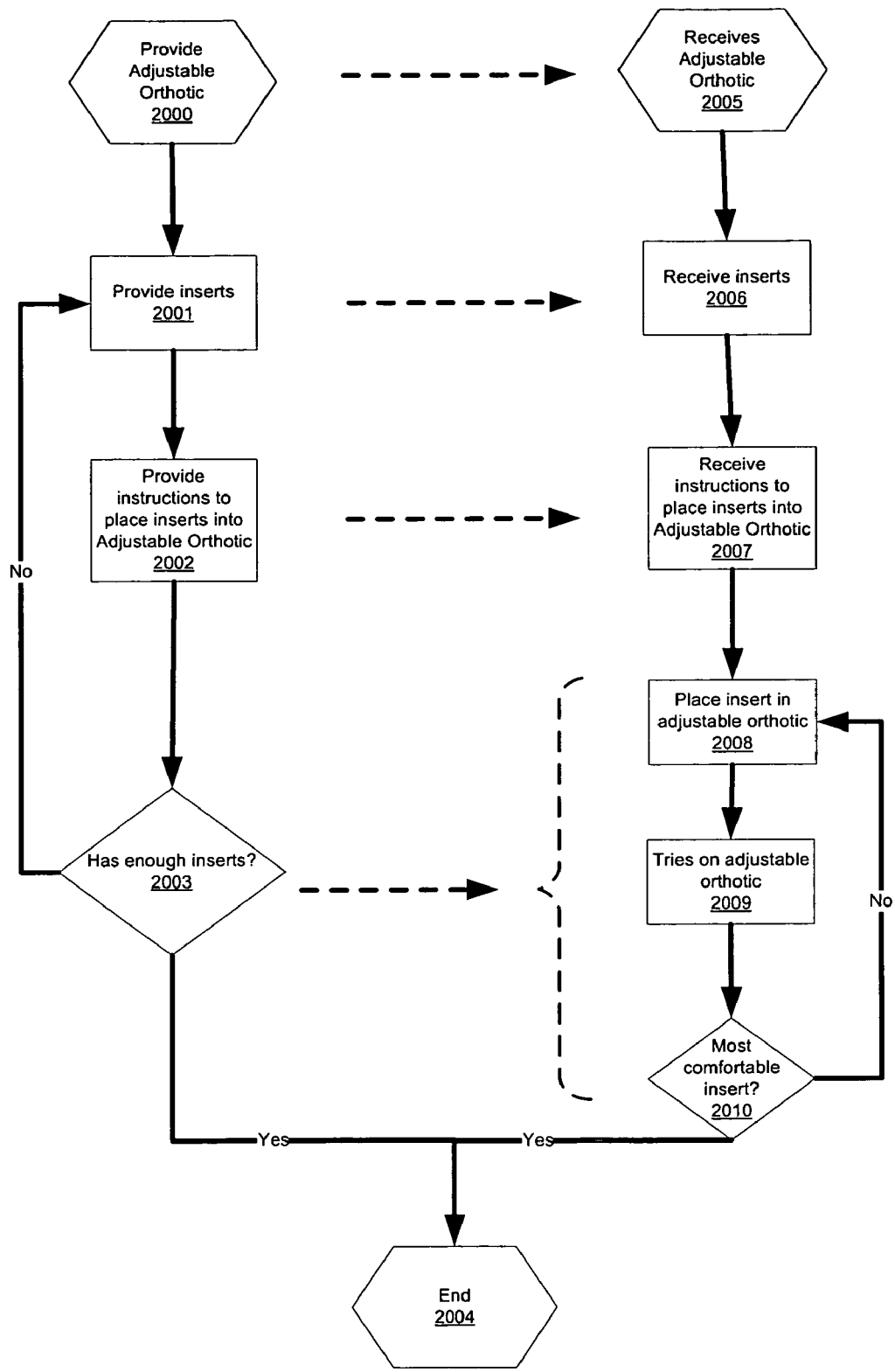
FIG. 20 illustrates a flowchart of an example procedure for providing a user customized fit for an orthotic, according to an example embodiment of the present invention.

FIG. 20 illustrates a flowchart of an example procedure for providing a user customized fit for an orthotic, according to an example embodiment of the present invention. In 2000, an adjustable orthotic that is configured to receive a removable insert that alters an amount of support provided by the orthotic may be provided to a user. In 2001, a set of inserts with different properties may be provided to a user, the inserts may be received by the orthotic. In 2002, instructions to select an insert from among the set of inserts which provides a user-preferred amount of support from the orthotic when the selected insert is inserted in the orthotic may be provided to a user. In 2003, a determination is made as to whether a user has enough inserts or if inserts do not adequately satisfy a user's needs. If not, 2001 is repeated and a user may be provided with more inserts. If the new inserts have different support properties or are dimensionally different than the prior inserts, 2002 may be repeated to teach the user how to place the inserts into the adjustable orthotic. Once the adjustable orthotic has been customized the insert search process may end 2004.

On the user end, in 2005, an adjustable orthotic may be received by a user. In 2006, inserts may be received by the user. In 2007, instructions to place inserts into the adjustable orthotic may be received by the user. In 2008, inserts may be placed into the adjustable orthotic by the user, as per the instructions received in 2007. In 2009, the adjustable orthotic with the inserts may be tried on by the user. In 2010, it is determined whether the adjustable orthotic support level is comfortable to the wearer. If the user is satisfied, the user selection process ends 2004. If the orthotic is not comfortable, steps 2008 to 2010 may be repeated until an insert is selected that provides the most comfort to a user.

Several example embodiments of the present invention are specifically illustrated and described herein. However, it will be appreciated that modifications and variations of the present invention are covered by the above teachings and within the purview of the appended claims without departing from the spirit and intended scope of the invention.

What is claimed is:

1. An orthotic, comprising:
   a foam cushioning layer configured to extend from the heel region of a user to at least the anterior metatarsal region of the user when the orthotic is in use;
   a supportive shell having a top surface and a bottom surface, the supportive shell harder than the foam cushioning layer and positioned beneath the foam cushioning layer, the supportive shell configured to extend longitudinally from at least the talus-navicular joint of the user to the medial cuneiform-first metatarsal joint of the user and laterally under at least the medial cuneiform bone of the user when the orthotic is in use, the supportive shell including an upturned flange on the medial side and an opening in the bottom surface configured to receive a removable insert; and
   a removable insert configured to be removably received in the opening, wherein the removable insert is harder than the shell layer, the insert altering the support properties of the orthotic when it is received in the opening, the insert when received in the opening extending longitudinally from at least the talus-navicular joint of the user to the medial cuneiform-first metatarsal joint of the user when the orthotic is in use.

2. An orthotic, comprising:
   a cushioning layer;
   a shell layer disposed under the cushioning layer;
   the shell layer configured to extend longitudinally from at least the talus-navicular joint of a user to the medial cuneiform-first metatarsal joint of a user and laterally under at least the medial cuneiform bone of the user when the orthotic is in use;
   the shell layer configured to receive a removable insert that alters the support provided by the orthotic; and
   a removable insert configured to be received by the shell layer, the removable insert altering support provided by the orthotic when the removable insert is received by the shell layer, wherein the removable insert is harder than the shell layer.

3. An orthotic, comprising:
   a cushioning layer;

a shell layer disposed under the cushioning layer;

the shell layer configured to extend longitudinally from at least the talus-navicular joint of a user to the medial cuneiform-first metatarsal joint of a user and laterally under at least the medial cuneiform bone of the user when the orthotic is in use;

the shell layer configured to receive a removable insert that alters the support provided by the orthotic; and a removable insert configured to be received by the shell layer, the removable insert altering support provided by the orthotic when the removable insert is received by the shell layer, wherein the removable insert is more rigid than the shell layer.

4. An orthotic, comprising:

a cushioning layer;

a shell layer disposed under the cushioning layer;

the shell layer configured to extend longitudinally from at least the talus-navicular joint of a user to the medial cuneiform-first metatarsal joint of a user and laterally under at least the medial cuneiform bone of the user when the orthotic is in use;

the shell layer configured to receive a removable insert that alters the support provided by the orthotic; and a removable insert configured to be received by the shell layer, the removable insert altering support provided by the orthotic when the removable insert is received by the shell layer, wherein the removable insert includes a substantially flat body with protruding ribs.

5. The orthotic of claim 4, wherein the protruding ribs extend longitudinally along the substantially flat body.

6. The orthotic of claim 4, wherein the protruding ribs are shaped to curve away from each other.

7. An orthotic, comprising:

a cushioning layer;

a shell layer disposed under the cushioning layer;

the shell layer configured to extend longitudinally from at least the talus-navicular joint of a user to the medial cuneiform-first metatarsal joint of a user and laterally under at least the medial cuneiform bone of the user when the orthotic is in use;

the shell layer configured to receive a removable insert that alters the support provided by the orthotic;

a removable insert configured to be received by the shell layer, the removable insert altering support provided by the orthotic when the removable insert is received by the shell layer;

the removable insert further comprising insertion tabs; and the shell layer further comprising apertures configured to receive the insertion tabs;

wherein the insertion tabs, when inserted in apertures in shell layer, removably retain the removable insert in the shell layer.

\* \* \* \* \*